United States Patent [19]
Lee et al.

[11] Patent Number: 5,916,555
[45] Date of Patent: Jun. 29, 1999

[54] PHARMACEUTICAL COMPOSITION FOR TREATMENT OF DIABETES

[75] Inventors: Jung Sik Lee, Seoul, Rep. of Korea;
Chung San Kong, Namganggu, China;
Song Deuk Lee; Kyung Eun Kwak,
both of Seoul, Rep. of Korea

[73] Assignee: Sam Chun Dang Pharm Co., Ltd.,
Seoul, Rep. of Korea

[21] Appl. No.: 08/961,069

[22] Filed: Oct. 30, 1997

[30] Foreign Application Priority Data

Nov. 1, 1996 [KR] Rep. of Korea ................. 96-51572

[51] Int. Cl.$^6$ ............ A61K 35/70; A61K 35/38; A61K 35/56; A61K 35/78
[52] U.S. Cl. ............ 424/93.5; 424/537; 424/538; 424/551; 424/520; 424/539; 424/195.1
[58] Field of Search ................. 424/93.5, 537, 424/538, 551, 520, 195.1, 539

[56] References Cited

U.S. PATENT DOCUMENTS

| 4,518,591 | 5/1985 | Iida et al. ............... 424/195.1 |
| 5,190,757 | 3/1993 | Kim ........................ 424/195.1 |
| 5,318,798 | 6/1994 | Uchida et al. ............. 427/213.35 |

OTHER PUBLICATIONS

Chemical Abstracts 117(5):40020x (1992).
Chemical Abstracts 122(1):1037s (1995).
Chemical Abstracts 124(15):193330t (1996).
Chemical Abstracts 127:30329 (1997).

*Primary Examiner*—Francisco Prats
*Attorney, Agent, or Firm*—Birch, Stewart, Kolasch & Birch, LLP

[57] ABSTRACT

The present invention relates to a pharmaceutical composition containing a combination of natural drugs for treatment of diabetes. More specifically, the present invention relates to a composition containing 17 kinds of main natural drugs, i. e. Cordyceps, *Bezoar bovis, Carthami flos, Astragali radix,* Hirudo, *Polygoni cuspidati radix, Polygonati falcati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmaniae radix crudae*. In addition to 17 kinds of main natural drugs, if desired, the composition of the present invention can contain one or more supplementary natural drugs selected from the group consisting of *Liriopsis tuber, Cistanchis herba, Adenophorae radix, Salviae radix, Ginseng radix rubra, Anemarrhenae rhizoma, Pachymae fungus, Phellodendri cortex, Mori radicis cortex, Schizandrae fructus, Galli stomachichum corium, Trichosanthis radix, Rhei rhizoma, Dioscoreae rhizoma, Alisma rhizoma, Polygoni multiflori radix, Galla rhois, Formica fusca L., Sanchi ginseng,* Margaritum and Gecko. The composition of the present invention is an agent for prevention of diabetes and for prevention and treatment of complications concomitant with diabetes by decreasing the blood sugar level of diabetic patients, but not decreasing the blood sugar level of normal person, and decreasing the blood lipid level, and therefore, is particularly effective for treatment of noninsulin-dependent diabetes (Type II diabetes) as well as insulin-dependent diabetes (Type I diabetes).

11 Claims, No Drawings

PHARMACEUTICAL COMPOSITION FOR TREATMENT OF DIABETES

BACKGROUND OF THE INVENTION

1. Field of the Invention

The present invention relates to a pharmaceutical composition containing a combination of natural drugs for treatment of diabetes. More specifically, the present invention relates to a composition containing 17 kinds of main natural drugs, i. e. Cordyceps, *Bezoar bovis, Carthami flos, Astragali radix,* Hirudo, *Polygoni cuspidati radix, Polygonati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmaniae radix crudae,* which is an agent for prevention of diabetes and for prevention and treatment of complications concomitant with diabetes by decreasing the blood sugar level of diabetic patients, but not decreasing the blood sugar level of normal person, and decreasing the blood lipid level. The composition of the present invention is particularly effective for treatment of noninsulin-dependent diabetes (Type II diabetes) as well as insulin-dependent diabetes (Type I diabetes).

2. Background Art

Recently, due to a high economical growth and an improvement and westernization in the standard of living, body development of the younger generation shows very preferable result. However, in adult men diseases have been gradually westernized due to excessive intake of high calorie food, lack of exercise and stress resulting from complex industrial society. Typical example of adult diseases includes hypertension, diabetes, obesity, hyperlipidemia (hypercholesteremia), etc. Particularly, diabetes is regarded as the origin of all chronic vascular diseases.

In Korea, although before the 1970's diabetic patient occupies merely about 0.5% of national population which does not arise the medical interest, it is assumed that diabetic patient has increase to 2–3% in the 1980's and 4–6% of national population in the 1990's. Many of diabetic patients live without knowing that they suffer from diabetes. Diabetes itself may not be regarded as being a serious disease but is considered as a social problem since diabetes causes numerous complications, for example, diabetic neuropathy, retinopathy, cataract, nephropathy, etc., which make diabetic patients not to lead a normal life and may cause fetal result in the end.

Diabetes is a disease wherein glucose is not utilized as an energy source in the body and is remained at a high level in blood and then excreted through urine, since insulin secreted from β cells of pancreas is insufficient or does not sufficiently fulfil its function.

Diabetes is generally classified into insulin-dependent diabetes (Type I diabetes) and noninsulin-dependent diabetes (Type II diabetes). Type I diabetes is in the state of lowering of the function of pancreatic β cells resulting from hereditary cause, viral infection, etc. wherein insulin is substantially not secreted, and suddenly attacks mainly in the twenties to thirties. Although it is not sure, type II diabetes mainly attacks in the forties and after due to family history for diabetes, obesity, stress, etc. In the case of type II diabetes, since insulin is sufficiently secreted from pancreas but insulin resistance and glucose utilization are different from those of normal person, blood sugar is not returned to normal level in spite of hyperinsulinemia.

Diabetes is accompanied with numerous symptoms. Typical examples of such symptoms are polyuria, excessive drinking and polyphagia. That is, diabetic patients exhibit polyuria which is caused by excretion of glucose and excessive water through urine by the action of osmotic pressure originated from high blood glucose level, and therefore, complain of thirst caused by dehydration, which induces excessive drinking, and feels the empty of stomach to cause excessive intake of food. Diabetic patients cannot efficiently utilize glucose as an energy source and, instead, utilize protein and fat as preserved in the body, and this phenomenon is caught in a vicious circle to cause the reduce of body weight.

However, such phenomena are merely the acute symptoms shown in the primary stage of diabetes. If diabetes becomes chronic by delay of treatment, chronic vascular diseases are induced as a complication. Thus, diabetic complications such as diabetic retinopathy (visual disturbance, blindness, retinal hemorrhage), diabetic nephropathy, diabetic peripheral neuropathy, etc. reduce general metabolic and sensory function of human body.

In view of eastern medical science, diabetes can be classified into three kinds of weakness, i. e. weakness at high part, middle part and lower part of human body, of which the cause is fever of lung, stomach and kidney, respectively. Weakness at high part is merely called a disease symptomized by thirst, which is characterized in that heart is weak to transfer bad fever to lung and therefore, the patient feels dry in the chest, tongue is red and the lips are dry to cause excessive drinking. Weakness at middle part has polyuria and polyphagia as the main symptom and leads to the loss of body weight and the constipation due to a vicious circle of polyuria and polyphagia. Weakness at lower part is also called weakness of kidney. In the case of weakness at lower part, thirst is less than that in weakness at high part and the volume of urine is large and the pulse is weak. Weakness at high part, which has a serious thirst as the main symptom, may be well treated, but weakness at middle and lower parts is difficult to treat. When thirst lessens and body weight rapidly decreases, this means the progress of diabetes toward weakness at lower part.

The agent for treatment of diabetes which has been frequently used in recent days is generally classified into oral hypoglycemic agents and insulin injections. In general, insulin injection preparations are administered to patients suffering from insulin-dependent diabetes, pregnancy diabetes, and noninsulin-dependent diabetes which is difficult to control blood sugar with oral hypoglycemic agent; and oral hypoglycemic agents are administered to patients suffering from noninsulin-dependent diabetes wherein blood sugar cannot be appropriately controlled in spite of the combination of dietary therapy and exercise therapy.

Commonly used oral hypoglycemic agent can be classified into sulfonylurea-based drugs, biguanide-based drugs and Chinese medicines. Sulfonylurea-based drugs include glypizide, glyclazide, glyquidone, glybenclamide, chlorpropamide, etc., which exhibit stimulation of insulin secretion from pancreas. Therefore, these drugs have disadvantages that they cannot be used for insulin-dependent diabetes wherein insulin is never secreted from pancreas, and further for noninsulin-dependent diabetes wherein insulin secretion from pancreas is relatively reduced, and for women who has a possibility of pregnancy, since they may cause delivery of deformed baby (giant baby), abortion, stillbirth, etc. In addition, when they are administered in an excessive dosage or on an empty stomach, they may cause hypoglycemia and exhibit side effects such as skin rash, jaundice, anorexia, nausea (vomiting), diarrhea, etc. Particularly, the agent having long half-life (12 to 18 hours)

such as chlorpropamide may be accumulated in the body and therefore, is very highly possible to cause hypoglycemia. In addition, since sulfonylurea-based drugs are metabolized in liver and excreted through kidney, they should be administered to patients accompanying disorder of liver and kidney function only with considerable care.

Typical example of biguanide-based drugs includes methpormine, etc. However, it is disclosed that their acting mechanism is not identified as yet but they do not have an effect of increasing insulin secretion from pancreas. Biguanide-based drugs show lower effect of reducing blood sugar level than that of sulfonylurea-based drugs and, instead, has a little possibility of hypoglycemia. But, they frequently cause gastrointestinal side-effects. Specifically, at the initial stage of treatment with biguanide-based drugs nausea, vomiting, diarrhea, rash, etc. may exhibit, and further, biguanide drugs may induce lactic acidosis to cause fatal side-effects. Therefore, in America the use of biguanide drugs has been limited to the experimental purpose.

Chinese medicines which have recently used for treatment of diabetes are differently prescribed depending on three kinds of weakness. For weakness at high part wherein lung has a fever, tongue is red and thirst is serious, "Insambaekhotang" (Gypsum, *Anemarrhenae rhizoma, Ginseng radix, Glycyrrhizae radix*), "Junssibaekchultang" (dried *Puerariae radix, Ginseng radix, Atractylodis rhizoma alba*, Hoelen, *Saussureae radix, Agastachis herba, Glycyrrhizae radix*), etc. can be used.

For weakness at middle part wherein due to the fever of stomach digestion is poor, faeces is hard to have frequent calls of nature, but not to obtain fresh feeling, "Chowiseungkitang" (*Rhei rhizoma, Natrii sulfas, Glycyrrhizae radix*), "Sangjingamroeum" (Gypsum, *Phellodendri cortex, Astragalli radix, Anemarrhenae rhizoma, Carthami flos, Bupleuri radix*, etc.) which is disclosed in "Dongeubogam", etc. can be used.

For weakness at lower part wherein due to the fever of kidney renal fluid is deficient, resinous body fluid is exhausted and thirst is less than that in case of weakness at high part and the lower belly above the bladder (e. g. kidney, liver) is chill, "Yukmijiwhangwhan" (steamed *Rehmaniae radix, Dioscoreae rhizoma, Corni fructus,* Hoelen, *Moutan cortex, Alisma rhizoma*), "Shingiwhan", etc. can be used.

However, in most of diabetic patients all of three kinds of weakness simultaneously occur although each of weaknesses at high, middle and lower parts may separately occur. Therefore, in most cases, diabetic patients suffering from all of three kinds of weakness cannot be effectively treated with the above-mentioned Chinese medicines as conventionally used.

Thus, the present inventors have extensively studied to find the composition which can be effectively used for treatment of diabetic patients suffering from all of three kinds of weakness, by variously combining natural drugs which have been disclosed as having relatively little side effects. In view of eastern medical science, diabetes can be treated by removing the fever from lung, stomach and kidney, preventing the spleen from wetting and reinforcing the spleen and kidney, and further by reducing blood lipid level, stimulating blood circulation, eliminating dryness and thirst and forming resinous body fluid.

In consideration of this, in order to find out a composition of natural drugs which satisfies all of the therapeutic guides as mentioned above to effectively treat diabetes having all of three kinds of weakness contrary to the prior Chinese medicines, the present inventors have conducted many experiments using compositions containing the various combination of natural drugs. As a result, we have identified that the composition of natural drugs as defined below can be attained the purpose as mentioned above, and completed the present invention.

Accordingly, the object of the present invention is to provide a composition of natural drugs which is useful for treatment of diabetes.

In addition, another object of the present invention is to provide a composition for treatment of diabetes, which contains 17 kinds of main natural drugs, i. e. Cordyceps, *Bezoar bovis, Carthami flos, Astragali radix,* Hirudo, *Polygoni cuspidati radix, Polygonati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmaniae radix crudae*.

The foregoing has outlined some of the more pertinent objects of the present invention. These objects should be construed to be merely illustrative of some of the more pertinent features and applications of the invention. Many other beneficial results can be obtained by applying the disclosed invention in a different manner of modifying the invention within the scope of the disclosure. Accordingly, other objects and a more thorough understanding of the invention may be had by referring to the disclosure of invention, in addition to the scope of the invention defined by the claims.

DISCLOSURE OF THE INVENTION

The present invention relates to a composition of natural drugs which is useful for treatment of diabetes.

More specifically, the present invention relates to a composition for treatment of diabetes, which contains 17 kinds of main natural drugs, i. e. Cordyceps, *Bezoar bovis, Carthami flos, Astragali radix,* Hirudo, *Polygoni cuspidati radix, Polygonati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmaniae radix crudae*.

The composition of the present invention which comprises the combination of 17 kinds of main natural drugs as defined above can exhibit simultaneously numerous pharmacological actions of main natural drugs so that it can be suitably treated various symptoms caused by diabetes having three kinds of weakness, and has substantially no side effect. Therefore, the composition of the present invention can be effectively used as an agent for treatment of diabetes.

Hereinafter, the complex effect of the composition of the present invention for treatment of diabetes, which is originated from the pharmacological activities of main natural drugs is specifically explained.

Since diabetes is a metabolic wasting disease, diabetic patients are in the conditions that all functions of the body is depressed and energy is weakened, in the composition of the present invention *Astragali radix* and *Atractylodis rhizoma alba* which are typical energy supplement agents are added to reinforce the spleen and heighten the spleen energy.

*Astragali radix* has a potent action of forming resinous body fluid and lowering the fever of spleen and lung to remove the thirsty feeling. *Atractylodis rhizoma alba* has a bitter taste and therefore, exhibits blood sugar lowering effect by removing the moisture from spleen and stomach and reinforcing the weakened function of spleen. For treating diabetes, although it is important to lower the high blood sugar level to the normal level, the action of continuously maintaining the normalized blood sugar level is also very important. Therefore, in the composition of the present invention *Atractylodis rhizoma* is added as a component for maintaining the normal blood sugar level. Differently from *Atractylodis rhizoma alba*, *Atractylodis rhizoma* has an action of maintaining the function of spleen and therefore, preserves the normalized blood sugar level.

The composition of the present invention contains *Puerariae radix* as a component for removing thirst. Such effect of *Puerariae radix* can be seen from "Shinnongkyungchobon" disclosing that *Puerariae radix* controls thirst, fever of whole body, vomiting, various paralysis, etc., and removes the effect of numerous poison by raising negative body energy; and "Myungeuibyulrok" disclosing that *Puerariae radix* treats the damage by thirst and coldness and the exhaustion by hot weather. In addition, *Puerariae radix* has an action of stimulating and increasing the positive energy of spleen and stomach.

Among the main natural drugs, *Moutan cortex, Lycii cortex radicis, Lycii fructus, Corni fructus* and *Rehmaniae radix crudae* have an action of producing the negative energy of kidney and reinforcing the kidney to effectively treat the weakness at lower part. In "Bonchogangmok" it is disclosed that *Moutan cortex* treats latent fever of blood and removes a febrile disease. Thus, *Moutan cortex* can treat and prevent diabetic vascular diseases by reducing blood fever and removing extravasated blood. *Lycii cortex radicis* has an action of reinforcing the kidney, removing fever, forming resinous body fluid and eliminating thirsty feeling to treat the weakness at high part. The activity of *Lycii cortex radicis* can be strengthened by combining with *Rehmaniae radix crudae, Trichosanthis radix, Schizandrae fructus,* etc. *Lycii fructus* reinforces the kidney to assist the formation of semen and treat the spermatorrhea due to loss of virility, makes the lung plentiful and has an action of reinforcing the liver to make the eyesight good.

Since *Corni fructus* has an action of warming the liver and an astringent action, it can be used for treatment of spermatorrhea, enuresis, etc. *Rehmaniae radix crudae* acts mainly on the heart, liver and kidney, has a potent nutritive and blood cleaning activity and is effective for treatment of loss of resinous body fluid and thirst caused by diabetes. As the prior Chinese medicines containing *Rehmaniae radix crudae* which were previously used for treatment of thirst, "Ikwitang" which contains *Liriopsis tuber* and *Adenophorae radix* in addition to *Rehmaniae radix crudae,* "Jachoieum" which contains *Corni fructus, Astragali radix, Dioscoreae rhizoma,* etc., in addition to *Rehmaniae radix crudae,* and the like can be mentioned.

Differently from *Rehmaniae radix crudae* which reinforces the weakened kidney and stimulates the semen and blood, *Polygonati falcati rhizoma* can be used to treat the weakness at high and middle parts by reinforcing the spleen and making the lung plentiful. Particularly, the activity of *Polygonati falcati rhizoma* can be strengthened by combining with *Astragali radix.* According to the animal experiment using rabbit, it has been confirmed that *Polygonati falcati rhizoma* directly acts on the blood vessel to reduce the blood pressure and blood lipid level, is effective for treatment of atherosclerosis and exhibits an action of reducing high blood sugar level caused by the lowering of kidney function.

*Polygoni cuspidati radix* exhibits an anti-viral activity. Due to such anti-viral activity, *Polygoni cuspidati radix* can prevent and treat the loss of pancreatic cell function caused by virus, etc., and therefore, reduce the occurrence and mortality of diabetes. This has also been reported on Chinese Journal "Bokgounyakmulji" in the year 1979.

Since Hirudo has a bitter taste to dry the moisture of spleen and remove extravasated blood to improve the blood circulation, it can be used for treatment of peripheral blood circulation disorder caused by diabetes.

Cordyceps acts on the kidney to improve all symptoms of weakness. In addition, since the activity of Cordyceps does not lean to any of negative and positive conditions, Cordyceps is incorporated in the composition of the present invention as an agent for counterbalancing the virile powers which can be used regardless of physical constitution of patients.

*Coptidis rhizoma* mainly acts on the organs positioned on the middle part (spleen, stomach, colon) and has a very bitter and cold pharmacological property. Therefore, since the cold property of *Coptidis rhizoma* can remove the fever of spleen and stomach and the bitter taste thereof can dry the moisture condition, *Coptidis rhizoma* can be used for treatment of the weakness at middle part. This has been disclosed in "Jinjoonang".

Since *Carthami flos* has a blood destructing activity when it is used in an excessive amount but has a blood nutritive activity at the small amount, it can improve the blood circulation in the whole body and particularly, improves the renal function by dilating the renal blood vessel.

It has been identified that the extract of *Euonymi lignum suberalatum* has an effect of lowering blood sugar level in rabbit. Such effect is caused by the activity of *Euonymi lignum suberalatum* for proliferating pancreatic $\beta$ cells and withdrawing $\alpha$ cells to induce an increase in insulin secretion.

*Bezoar bovis* is a typical blood cleaning and detoxicating agent used in the field of Chinese medicine and therefore, is used for improving the febrile feeling caused by diabetes in the composition of the present invention.

As mentioned above, the composition of the present invention exhibits a combination of numerous activities originated from main natural drugs. Therefore, contrary to the prior Chinese medicines having an effect of treating any one of three kinds of weakness, the composition of the present invention can remove the original cause of diabetes and strengthen the body function weakened due to diabetes, and therefore, can exhibit an excellent effect of treating diabetes having any kind of symptoms.

In the composition of the present invention, the main natural drugs are combined in the ratio of Cordyceps 0.1–5, *Bezoar bovis* 0.01–1, *Carthami flos* 0.5–5, *Astragali radix* 10–20, Hirudo 1–10, *Polygoni cuspidati radix* 5–15, *Polygonati falcati rhizoma* 10–20, *Euonymi lignum suberalatum* 10–20, *Corni fructus* 10–20, *Moutan cortex* 10–20, *Lycii cortex radicis* 10–20, *Lycii fructus* 10–20, *Atractylodis rhizoma alba* 5–15, *Atractylodis rhizoma* 10–20, *Coptidis rhizoma* 5–15, *Puerariae radix* 10–20 and *Rehmaniae radix crudae* 10–20, on the basis of dry weight. Preferably, in the composition of the present invention, the main natural drugs can be combined in the ratio of Cordyceps 0.5–2, *Bezoar bovis* 0.05–0.2, *Carthami flos* 2–3, *Astragali radix* 13–18, Hirudo 3–7, *Polygoni cuspidati radix* 8–12, *Polygonati rhizoma* 13–18, *Euonymi lignum suberalatum* 13–18, *Corni fructus* 13–18, *Moutan cortex* 13–18, *Lycii cortex radicis* 13–18, *Lycii fructus* 13–18, *Atractylodis rhizoma alba* 8–12, *Atractylodis rhizoma* 13–18, *Coptidis rhizoma* 8–12, *Puerariae radix* 13–18 and *Rehmaniae radix crudae* 13–18, on the basis of dry weight. Most preferably, the composition of the present invention contains the main natural drugs in the ratio of Cordyceps:*Bezoar bovis*:*Carthami flos*:*Astragali radix*:Hirudo:*Polygoni cuspidati radix*:*Polygonati rhizoma*:*Euonymi lignum suberalatum*:*Corni fructus*:*Moutan cortex*:*Lycii cortex radicis*:*Lycii fructus*:*Atractylodis rhizoma alba*:*Atractylodis rhizoma*:*Coptidis rhizoma*:*Puerariae radix*:*Rehmaniae radix crudae*= 1:0.1:2.5:15:5:10:15:15:15:15:15:15:10:15:10:15:15. The above ratio is established in consideration of effective amounts and side effects of each main natural drug. If the combination ratio is beyond the above range, the pharmacological effect may be rapidly reduced or any side effect may occur.

In order to obtain more potent hypoglycemic activity, if desired, the composition of the present invention can additionally contain one or more supplementary natural drugs selected from the group consisting of *Liriopsis tuber*, *Cistanchis herba*, *Adenophorae radix*, *Salviae radix*, *Ginseng radix rubra*, *Anemarrhenae rhizoma*, *Pachymae fungus*, *Phellodendri cortex*, *Mori radicis cortex*, *Schizandrae fructus*, *Galli stomachichum corium*, *Trichosanthis radix*, *Rhei rhizoma*, *Dioscoreae rhizoma*, *Alisma rhizoma*, *Polygoni multiflori radix*, *Galla rhois*, *Formica fusca L.*, *Sanchi ginseng*, Margaritum and Gecko.

When the supplementary natural drugs are added to the composition of the present invention, on the basis of dry weight, each of *Liriopsis tuber*, *Adenophorae radix*, *Trichosanthis radix*, *Cistanchis herba*, *Salviae radix*, *Polygoni multiflori radix*, *Mori radicis cortex*, *Anemarrhenae rhizoma*, *Alisma rhizoma*, *Schizandrae fructus*, *Pachymae fungus*, *Formica fusca L.*, *Galli stomachichum corium*, *Phellodendri cortex* and Gecko can be added in the ratio of 5–15 parts by weight, preferably of 8–12 parts by weight; each of Ginseng radix rubra, *Rhei rhizoma* and *Galla rhois* can be added in the ratio of 1–10 parts by weight, preferably of 3–7 parts by weight; each of Margaritum and *Sanchi ginseng* can be added in the ratio of 0.5–5 parts by weight, preferably of 2–3 parts by weight; and *Dioscoreae rhizoma* can be added in the ratio of 10–20 parts by weight, preferably of 13–18 parts by weight.

The composition of the present invention can be prepared according to the method conventionally used in the pharmaceutical field. For example, Cordyceps and, if desired, Ginseng radix rubra, Margaritum, Gecko and *Formica fusca L.* are pulverized and then sieved to obtain the fine powders thereof, and *Bezoar bovis* is also thoroughly ground to obtain the fine powder thereof. *Atractylodis rhizoma alba*, *Moutan cortex* and *Atractylodis rhizoma* are distilled to extract the volatile essence components which are then mixed with cyclodextrin and ethanol, and the obtained mixture is ground, dried and then more finely ground again to obtain the fine powder. To the residue obtained after *Atractylodis rhizoma alba*, *Moutan cortex* and *Atractylodis rhizoma* are distilled to extract the volatile essence component is added water and the mixture is filtered to separate the aqueous solution. The remaining residue is mixed with *Carthami flos*, *Astragali radix*, Hirudo, *Polygoni cuspidati radix*, *Polygonati rhizoma*, *Euonymi lignum suberalatum*, *Corni fructus*, *Lycii cortex radicis*, *Lycii fructus*, *Coptidis rhizoma*, *Puerariae radix*, *Rehmaniae radix crudae* and, if desired, *Liriopsis tuber*, *Cistanchis herba*, *Adenophorae radix*, *Salviae radix*, *Anemarrhenae rhizoma*, *Pachymae fungus*, *Phellodendri cortex*, *Mori radicis cortex*, *Schizandrae fructus*, *Galli stomachichum corium*, *Trichosanthis radix*, *Dioscoreae rhizoma*, *Alisma rhizoma*, *Polygoni multiflori radix*, *Rhei rhizoma*, *Sanchi ginseng* and *Galla rhois*. The resulting mixture is boiled two times for 2 hours each time, and combined with the aqueous solution of *Atractylodis rhizoma alba*, *Moutan cortex* and *Atractylodis rhizoma* as separated above. The combined solution is filtered and the filtrate is concentrated preferably to obtain the specific gravity of about 1.0–1.20. To the resulting concentrate is added ethanol, and the mixture is allowed to stand and then filtered. The filtrate is again concentrated. The obtained concentrate is mixed with the powder components as obtained above to obtain the desired composition of the present invention.

In using the composition of the present invention for the clinical purpose of treating diabetes, the composition can be formulated according to the conventional method used in the pharmaceutical field into the oral dosage form, for example, pills, tablets, capsules, solutions, suspensions, etc.

Although the dosage of the composition of the present invention to be administered to the patients who are in need of treating diabetes can be suitably selected depending on sex, age, health condition of the patient, kinds and severity of diabetes to be treated, complications, etc., the daily dosage for adult man (body weight ca. 70kg) is generally 2–6g and preferably 3–5g.

The present invention is more specifically explained by the following examples and experiments. However, it should be understood that the present invention is not limited to these examples in any manner.

EXAMPLE 1

100 g of Cordyceps was pulverized to obtain the fine powder thereof (1), and 10 g of *Bezoar bovis* was also thoroughly ground to obtain the fine powder (2). 1000 g of *Atractylodis rhizoma alba*, 1500 g of *Moutan cortex* and 1500 g of *Atractylodis rhizoma* were distilled to extract the volatile essence components. The extract was then mixed with 5 g of cyclodextrin and 15 l of ethanol, and the obtained mixture is ground, dried and then more finely ground again to obtain the fine powder (3). To the residue obtained after *Atractylodis rhizoma alba*, *Moutan cortex* and *Atractylodis rhizoma* was distilled to extract the volatile essence component was added water and the mixture was filtered to separate the aqueous solution. The remaining residue was mixed with 12 kinds of natural drugs, i. e. 250 g of *Carthami flos*, 1500 g of *Astragali radix*, 500 g of Hirudo, 1000 g of *Polygoni cuspidati radix*, 1500 g of *Polygonati rhizoma*, 1500 g of *Euonymi lignum suberalatum*, 1500 g of *Corni fructus*, 1500 g of *Lycii cortex radicis*, 1500 g of *Lycii fructus*, 1000 g of *Coptidis rhizoma*, 1500 g of *Puerariae radix* and 1500 g of *Rehmaniae radix crudae*. The resulting mixture was boiled two times for 2 hours each time, and then combined with the aqueous solution of *Atractylodis rhizoma alba*, *Moutan cortex* and *Atractylodis rhizoma* as separated above. The combined solution is filtered and the filtrate is concentrated to obtain the specific gravity of about 1.0–1.20. To the resulting concentrate was added ethanol to prepare 75% alcoholic solution which was then allowed to stand for 12 hours and then filtered. The filtrate was again concentrated to obtain the concentrate in a plaster state (4). The obtained (1), (2), (3) and (4) were mixed together to obtain 2.7kg of the desired natural drug composition according to the present invention.

EXAMPLE 2

100 g of Cordyceps was ground to obtain the fine powder thereof (1), and 10 g of *Bezoar bovis* was also thoroughly ground to obtain the fine powder (2). Separately, 500 g of

*Ginseng radix rubra,* 1000 g of *Formica fusca L.,* 250 g of Margaritum and 1000 g of Gecko were ground and then sieved to obtain the fine powder (3). 1000 g of *Atractylodis rhizoma alba,* 1500 g of *Moutan cortex* and 1500 g of *Atractylodis rhizoma* were distilled to extract the volatile essence components. The extract was then mixed with 5 g of cyclodextrin and 15 l of ethanol, and the obtained mixture was ground, dried and then more finely ground again to obtain the fine powder (4). To the residue obtained after *Atractylodis rhizoma alba, Moutan cortex* and *Atractylodis rhizoma* were distilled to extract the volatile essence component was added water and the mixture was filtered to separate the aqueous solution. The remaining residue was mixed with 250 g of *Carthami flos,* 1500 g of *Astragali radix,* 500 g of Hirudo, 1000 g of *Polygoni cuspidati radix,* 1500 g of *Polygonati rhizoma,* 1500 g of *Euonymi lignum suberalatum,* 1500 g of *Corni fructus,* 1500 g of *Lycii cortex radicis,* 1500 g of *Lycii fructus,* 1000 g of *Coptidis rhizoma,* 1500 g of *Puerariae radix,* 1500 g of *Rehmaniae radix crudae,* 1000 g of *Liriopsis tuber,* 1000 g of *Cistanchis herba,* 1000 g of *Adenophorae radix,* 1000 g of *Salviae radix,* 1000 g of *Anemarrhenae rhizoma,* 1000 g of *Pachymae fungus,* 1000 g of *Phellodendri cortex,* 1000 g of *Mori radicis cortex,* 1000 g of *Schizandrae fructus,* 1000 g of *Galli stomachichum corium,* 1000 g of *Trichosanthis radix,* 1500 g of *Dioscoreae rhizoma,* 1000 g of *Alisma rhizoma,* 1000 g of *Polygoni multiflori radix,* 500 g of *Rhei rhizoma,* 250 g of *Sanchi ginseng* and 500 g of *Galla rhois.* The resulting mixture was boiled two times for 2 hours each time, and combined with the aqueous solution of *Atractylodis rhizoma alba, Moutan cortex* and *Atractylodis rhizoma* as separated above. The combined solution was filtered and the filtrate was concentrated to obtain the specific gravity of about 1.0–1.20. To the resulting concentrate was added ethanol to prepare 75% alcoholic solution which was then allowed to stand for 12 hours and then filtered. The filtrate was again concentrated to obtain the concentrate in a plaster state (5). The obtained (1), (2), (3), (4) and (5) were mixed together to obtain 5 kg of the desired natural drug composition of the present invention.

Experiment 1
Blood sugar lowering effect of the composition of the present invention To test the blood sugar lowering activity of the composition of the present invention, model animals for type I diabetes (insulin-dependent diabetes) and type II diabetes (noninsulin-dependent diabetes) were established. In all of the following experiments, the experimental animals were allowed to freely take the commercial mouse feed (constituents: corn, soybean, wheat, beef tallow, crude fat, crude ash, crude fiber, calcium, phosphorus, containing 25% or more of crude protein).

(1) Effect of lowering blood sugar level and on insulin concentration in the case of type I diabetes (insulin-dependent diabetes)

Type I diabetes is caused by lack of insulin secretion due to destruction of pancreatic β cells resulting from viruses or environmental factors. Therefore, 30 NOD mice were used as the experimental animal, wherein 10 mice constitute the normal group and the remaining 20 mice were established as type I diabetes model animal by intraperitoneally administering streptozotocin in an amount of 60 mg/kg/day for three consecutive days to lower the function of pancreas. Among 20 type I diabetes model animals, 10 mice constitute the control group which did not receive any drug and the remaining 10 mice were given the composition of the present invention. After the hyperglycemia was induced by repeatedly administering streptozotocin, the composition prepared in Example 1 according to the present invention was orally administered in an amount of 0.3 g/kg/day for two weeks from 6 days after the initial administration of streptozotocin. After 3 days, one and two weeks from administration of the composition of the present invention and on 3 and 4 weeks after the administration of the composition was suspended, blood was taken from orbital venous plexus of mouse at the point of 2 hours after administration of the composition of the present invention and was then subjected to measurement of blood sugar level by means of a glucose-meter. The obtained result is described in the following Table 1.

TABLE 1

Blood sugar level in type I diabetic model NOD mouse (unit = mg/dl)

| | Before administration | 3 days | one week | two weeks | three weeks | four weeks |
|---|---|---|---|---|---|---|
| Normal group (NOD/♂) | 150.8 ± 5.8 (n = 10) | — | 154.5 ± 6.7 (n = 10) | 150.5 ± 7.3 (n = 10) | 151.3 ± 5.6 (n = 10) | 153 ± 7.2 (n = 10) |
| Control group | 259.0 ± 4.3 (n = 10) | 326.4 ± 7.6 (n = 10) | 400.6 ± 5.9 (n = 10) | 420.7 ± 7.4 (n = 10) | 428.2 ± 5.5 (n = 10) | 431 ± 6.9 (n = 10) |
| Test group* (0.3 g/kg) | 264.0 ± 6.1 (n = 10) | 231.8 ± 8.8 (n = 10) | 211.3 ± 6.3 (n = 10) | 202.5 ± 9.7 (n = 10) | 180.6 ± 7.1 (n = 10) | 171 ± 7.5 (n = 10) |

Note)
(1) Test group = group receiving 0.3 g/kg of the composition of the present invention
(2) $P < 0.05$ In addition, in type I diabetic model NOD mouse wherein hyperglycemia was induced by streptozotocin according to the same procedure as above, the effect of the composition of the present invention on insulin concentration in serum was determined in an amount of 0.3 g/kg/day according to the following manner. Specifically, from three groups (normal group, control group and test group) of the experimental animals as used above, blood was taken from carotid artery of mouse at the point of 4 weeks after administration of the composition of the present invention and then subjected to measurement of serum insulin concentration by a radioimmunoassay. The obtained result is described in the following Table 2.

TABLE 2

Change of serum insulin concentration in streptozotocin-induced type I diabetic model mouse

|  | Insulin ($\mu$IU/ml) |
| --- | --- |
| Normal group (ICR) | 8.95 ± 1.2 (n = 10) |
| Control group | 7.42 ± 0.9 (n = 10) |
| Test group (0.3 g/kg of the composition of the present invention) | 9.04 ± 1.2 (n = 10) |

From the results described in the above Tables 1 and 2, it can be seen that the natural drug composition of the present invention can effectively lower the blood sugar level and increase the insulin concentration in type I diabetic model animal induced by administration of streptozotocin. Therefore, the composition of the present invention can be used as an effective agent for treatment of type I diabetes, i. e. insulin-dependent diabetes.

(2) Effect of lowering blood sugar level in the case of type II diabetes (non-insulin-dependent diabetes)

Although the definite mechanism of type II diabetes has not been established yet, in the case of type II diabetes the resistance of peripheral tissues against insulin increases due to obesity, etc., thereby hyperinsulinemia occurs. Since $\beta$ cells of type II diabetic patient has a reduced reactivity for insulin secretion due to increase in blood sugar level, the patients cannot recognize the excretion of sugar through urine and continuously secrete insulin. 20 $KKA^Y$ mice showing the symptoms as mentioned above were divided into two groups (control group and test group) wherein each group contains 10 mice. The control group was given only physiological saline in an amount of 10 ml/kg and the test group was given via oral route the composition prepared in Example 1 according to the present invention in an amount of 0.3 g/kg/day for 4 weeks. Blood was periodically taken from orbital venous plexus of mouse after 2 hours from administration of the test composition and the blood sugar level was measured by means of a glucose-meter. The obtained result is described in the following Table 3.

Using KK mouse as type II diabetic model animal, the blood sugar lowering effect of the composition of the present invention was compared with that of glyclazide which is a typical sulfonylurea-based agent for treatment of diabetes, according to the following method.

30 KK mice as type II diabetic model animal were divided into three groups comprising control group, first test group and second test group wherein each group was composed of 10 mice. The control group was given only physiological saline in an amount of 10 ml/kg, the first test group was given the composition of the present invention in an amount of 0.3 g/kg/day and the second test group was given glyclazide in an amount of 50 mg/kg/day, for 4 weeks in each group. Blood was taken from orbital venous plexus of mouse after 2 hours from administration of each of the test drugs and the blood sugar level was measured by means of a glucose-meter. The obtained result is described in the following Table 4.

TABLE 4

Blood sugar lowering effects of the composition of the present invention and glyclazide in type II diabetic animal (unit = mg/dl)

|  | Before administration | one week | two weeks | three weeks | four weeks |
| --- | --- | --- | --- | --- | --- |
| Control group (n = 10) | 183.1 ± 9.8 | 183.0 ± 10.4 | 172.4 ± 10.7 | 169.6 ± 8.1 | 178.9 ± 7.9 |
| First test group (n = 10) | 183.4 ± 7.6 | 157.7 ± 7.1 | 138.9 ± 7.9 | 133.5 ± 6.7 | 127.0 ± 6.6 |
| Second test group (n = 10) | 184.0 ± 7.1 | 149.4 ± 5.7 | 148.7 ± 10.1 | 140.1 ± 5.2 | 142.1 ± 6.0 |

Note)
(1) First test group = group receiving 0.3 g/kg of the composition of the present invention
(2) Second test group = group receiving 50 mg/kg of glyclazide From the result described in the above Table 4, it can be seen that the composition of the present invention exhibits a

TABLE 3

Blood sugar level in type II diabetic model $KKA^Y$ mouse (unit = mg/dl)

|  | Before administration | 3 days | one week | two weeks | three weeks | four weeks |
| --- | --- | --- | --- | --- | --- | --- |
| Control group (n = 10) | 161.0 ± 3.9 | 164.3 ± 11.9 | 165.0 ± 10.1 | 158.5 ± 9.6 | 160.7 ± 8.1 | 162.6 ± 7.8 |
| Test group* (n = 10) | 166.5 ± 5.6 | 139.0 ± 9.3 | 145.0 ± 7.7 | 131.0 ± 5.5 | 129.1 ± 4.7 | 120.2 ± 6.9 |

Note)
(1) Test group = group receiving 0.3 g/kg of the composition of the present invention
(2) P < 0.05

From the result described in the above Table 3, it can be seen that the composition of the present invention also exhibits a significant effect of lowering the blood sugar level in the case of noninsulin-dependent type II diabetes.

Experiment 2
Comparative test for effect of the composition of the present invention and glyclazide on blood sugar level more potent blood sugar lowering effect at the given amount in comparison to glyclazide which has been previously recognized as being an effective agent for treatment of diabetes.

Experiment 3
Comparative test for effect of the composition of the present invention and "Yukmijiwhangwhan" on blood sugar level The blood sugar lowering effect of the composition of the present invention was compared with that of "Yukmijiwhangwhan" (consisting of steamed *Rehmaniae radix, Dioscoreae rhizoma, Comi fructus,* Hoelen, *Moutan cortex* and *Alisma rhizoma*) which is a typical Chinese medicine for treatment of diabetes, according to the following method.

30 KK mice as type II diabetic (noninsulin-dependent diabetes) model animal were divided into three groups comprising control group, first test group and second test group wherein each group was composed of 10 mice. The control group was given only physiological saline in an amount of 10 ml/kg, the first test group was given the composition of the present invention in an amount of 0.3 g/kg/day and the second test group was given "Yukmijiwhangwhan" in an amount of 0.3 g/kg/day, for 5 weeks in each group. Blood was taken from orbital venous plexus of mouse and the blood sugar level was measured by means of a glucose-meter. The obtained result is described in the following Table 5.

except that one to three kinds of main natural drugs used in the composition of the present invention were deleted can exhibit the comparable effect to the composition of the present invention was examined.

Experiment 4

40 $KKA^Y$ mice as type II diabetic (noninsulin-dependent diabetes) model animal were divided into four groups wherein each group was composed of 10 mice. The control group was given only physiological saline in an amount of 10 ml/kg, the remaining three groups were given the composition prepared in Example 1 of the present invention (Group A), the composition prepared by combining 16 kinds of natural drugs according to the same method as Example 1 except that *Polygoni cuspidati radix* was deleted (Group B), and the composition prepared by combining 14 kinds of natural drugs according to the same method as Example 1 except that *Polygoni cuspidati radix,* and *Bezoar bovis* and Cordyceps, which strengthen the activity of *Polygoni cus-*

TABLE 5

Blood sugar lowering effects of the composition of the present invention and "Yukmijiwhangwhan"

(unit = mg/dl)

| | Before administration | one week | two weeks | three weeks | four weeks | five weeks |
|---|---|---|---|---|---|---|
| Control group (n = 10) | 184.2 ± 6.2 | 183.1 ± 9.8 | 172.6 ± 4.8 | 178.1 ± 5.2 | 169.6 ± 7.8 | 174.2 ± 6.2 |
| First test group (n = 10) | 185.7 ± 5.9 | 170.7 ± 7.6 | 156.1 ± 6.8 | 139.7 ± 8.1 | 130.5 ± 4.9 | 122.5 ± 7.8 |
| Second test group (n = 10) | 184.4 ± 7.1 | 187.6 ± 10.0 | 179.8 ± 10.0 | 172.2 ± 13.9 | 164.3 ± 14.6 | 170.3 ± 15.7 |

Note)
(1) First test group = group receiving 0.3 g/kg/day of the composition of the present invention
(2) Second test group = group receiving 0.3 g/kg/day of "Yukmijiwhangwhan"

From the result described in the above Table 5, it can be seen that the composition of the present invention exhibits a more potent blood sugar lowering effect in comparison to "Yukmijiwhangwhan" which is a prior Chinese medicine for treatment of diabetes.

In the following Experiments 4, 5 and 6, in order to demonstrate the superior therapeutic effect on diabetes obtained by combining 17 kinds of the main natural drugs in the composition according to the present invention, whether the natural drug compositions having the same constitution

*pidati radix* and reduce the diabetic fever, were deleted (Group C), respectively, and then their blood sugar lowering effects were compared with each other. After each composition was administered to the experimental animals for 4 weeks, blood was taken from orbital venous plexus of mouse and the blood sugar level was measured by means of a glucose-meter. The obtained result is described in the following Table 6.

TABLE 6

Blood sugar lowering effects (unit = mg/dl)

| | Before administration | one week | two weeks | three weeks | four weeks |
|---|---|---|---|---|---|
| Control group (n = 10) | 165.0 ± 4.6 | 163.6 ± 7.8 | 160.7 ± 8.1 | 165.0 ± 10.1 | 164.3 ± 7.6 |
| Group A (n = 10) | 166.1 ± 5.7 | 158.8 ± 6.9 | 146.7 ± 8.9 | 133.5 ± 7.7 | 125.2 ± 6.7 |
| Group B (n = 10) | 164.2 ± 7.3 | 155.2 ± 6.6 | 149.8 ± 5.8 | 140.1 ± 7.9 | 134.5 ± 10.2 |
| Group C (n = 10) | 164.0 ± 5.3 | 162.7 ± 7.7 | 158.3 ± 11.2 | 151.8 ± 8.2 | 150.7 ± 10.3 |

Experiment 5

30 KKA$^Y$ mice as type II diabetic (non insulin-dependent diabetes) model animal were divided into three groups wherein each group was composed of 10 mice. The control group was given only physiological saline in an amount of 10 ml/kg, the remaining two groups were given the composition prepared in Example 1 of the present invention (Group A) and the composition prepared by combining 15 kinds of natural drugs according to the same method as Example 1 except that Euonymi lignum suberalatum and *Bezoar bovis* were deleted (Group B), respectively, in an amount of 0.3 g/kg/day for 4 weeks, and then their blood sugar lowering effects were compared with each other. The obtained result is described in the following Table 7.

TABLE 7

|  | Before administration | one week | two weeks | three weeks | four weeks |
|---|---|---|---|---|---|
| | | | | | (unit = mg/dl) |
| Control group (n = 10) | 169.0 ± 6.5 | 167.1 ± 4.9 | 163.3 ± 8.1 | 165.5 ± 6.7 | 164.0 ± 9.1 |
| Group A (n = 10) | 168.7 ± 7.7 | 155.3 ± 8.8 | 149.4 ± 7.8 | 131.5 ± 7.4 | 125.2 ± 5.7 |
| Gorup B (n = 10) | 166.2 ± 6.8 | 157.4 ± 5.9 | 155.9 ± 9.2 | 146.2 ± 7.8 | 138.9 ± 9.0 |

According to the result of the above experiment using KKA$^Y$ mouse as noninsulin-dependent diabetic model animal, it can be seen that the composition having the same composition of the present invention except that Euonymi lignum suberalatum and Bezoar bovis are deleted exhibits somewhat little blood sugar lowering effect. In this case, it is assumed that the reason why the blood sugar lowering effect in Group B is not greatly different from that in Group A is that this experiment is carried out using noninsulin-dependent diabetic model animal which does not greatly influenced by insulin increased due to pancreatic β cell proliferation, as the experimental animal.

Experiment 6

In order to determine the effective dosage and the dosage range which can be administered to human patient, the composition of the present invention was administered to mouse in an amount as given in the following table and then the blood sugar lowering effect was measured.

As can be seen above, it is observed that the group to which the composition of the present invention was administered in an amount of 25 mg/kg/day (Group A) shows an effect of lowering the blood sugar level when the composition is administered for a long period, and the group to which the composition was administered in an amount of 90 mg/kg/day (Group B) exhibits the blood sugar lowering effect which is substantially equivalent to that of the group to which the composition was administered in an amount of 300 mg/kg/day (Group C).

From this result, it is considered that the dosage range of the composition of the present invention which can be administered to human patient is 2 to 6 g per day for adult man (average body weight 70 kg). The dosage may be increased or decreased depending on the symptoms accompanied by diabetes.

Experiment 7

Acute toxicity test

The LD$_{50}$ value of the composition of the present invention as the standard for acute toxicity was determined using mouse according to the following procedure. Before test, the experimental animal was fasted for one day.

50 ICR mice were used as the experimental animal and divided into 5 groups wherein each group contains 10 mice. Group A was given only physiological saline in an amount of 10 ml/kg and used as the control group. The composition of the present invention was administered in an amount of 10 g/kg/day for Group B, 30 g/kg/day for Group C, 60 g/kg/day for Group D, and 100 g/kg/day for Group E.

The animals belonging to Groups B to E were given the composition of the present invention in the form of a solution in physiological saline, via oral route. After 24 hours from oral administration of the composition of the present invention, the number of died animals was counted in each group. As a result, no died mouse was found in Groups B and C, one mouse was died in Group D and two mice were died in Group E.

In order to determine the LD$_{50}$ value the composition should be administered in an increased amount which kills 50% of the experimental animals, i. e. 5 mice. However, the composition of the present invention is hard to dissolve in water and therefore, if the composition is dissolved in an amount more than 100 g/kg, the volume of the composition is too large to administer to the experimental animal. Therefore, the toxicity test was conducted in the possible maximum amount of 100 g/kg.

As can be seen from the above experimental result, the composition of the present invention does not show side

TABLE 10

|  | Before administration | three days | one week | two weeks | three weeks |
|---|---|---|---|---|---|
| | | | | | (unit = mg/dl) |
| Control group (n = 10) | 189.5 ± 11.8 | 182.3 ± 14.8 | 193.3 ± 10.6 | 205.3 ± 10.5 | 207.5 ± 8.0 |
| Group A (n = 10) | 189.3 ± 7.0 | 171.8 ± 8.8 | 167.4 ± 4.1 | 159.9 ± 8.6 | 153.1 ± 8.5 |
| Group B (n = 10) | 186.8 ± 7.3 | 175.5 ± 7.2 | 164.0 ± 6.3 | 152.6 ± 7.4 | 148.0 ± 9.4 |
| Group C (n = 10) | 184.0 ± 7.6 | 166.5 ± 6.8 | 157.7 ± 7.1 | 138.9 ± 7.9 | 133.5 ± 10.7 |

Note)
Group A = group receiving 25 mg/kg/day of the composition of the present invention
Group B = group receiving 90 mg/kg/day of the composition of the present invention
Group C = group receiving 300 mg/kg/day of the composition of the present invention effects including hypoglycemia in any of Groups B, C, D and E, and therefore, it is assumed that the $LD_{50}$ value of the composition of the present invention is more than 100 g/kg. Since the dosage of 100 g/kg/day for mouse is converted into 7 kg or more per day for human patient on the basis of average body weight of 70 kg, it is concluded that the composition of the present invention is a safe drug which has substantially no side effect.

What is claimed is:

1. A composition for treatment of diabetes which comprises natural drugs Cordyceps, *Bezoar bovis, Carthami flos, Astragali radix,* Hirudo, *Polygoni cuspidati radix, Polygonati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmaniae radix crudae.*

2. The composition for treatment of diabetes according to claim 1, wherein Cordyceps, *Bezoar bovis, Carthami flos, Astragali radix,* Hirudo, *Polygoni cuspidati radix, Polygonati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmaniae radix crudae* are contained in the ratio of 0.1–5:0.01–1:0.5–5:10–20:1–10:5–15:10–20:10–20:10–20:10–20:10–20:10–20:5–15:10–20:5–15:10–20:10–20 on the basis of dry weight of natural drugs.

3. The composition for treatment of diabetes according to claim 2, wherein Cordyceps, *Bezoar bovis, Carthami flos, Astragali radix,* Hirudo, *Polygoni cuspidati radix, Polygonati rhizoma, Euonymi lignum suberalatum, Corni fructus, Moutan cortex, Lycii cortex radicis, Lycii fructus, Atractylodis rhizoma alba, Atractylodis rhizoma, Coptidis rhizoma, Puerariae radix* and *Rehmamiae radix crudae* are contained in the ratio of 1:0.1:2.5:15:5:10:15:15:15:15:15:15:10:15:10:15:15 on the basis of dry weight of natural drugs.

4. The composition for treatment of diabetes according to claim 1, which further comprises one or more supplementary natural drugs selected from the group consisting of *Liriopsis tuber, Cistanchis herba, Adenophorae radix, Salviae radix, Ginseng radix rubra, Anemarrhenae rhizoma, Pachymae fungus, Phellodendri cortex, Mori radicis cortex, Schizandrae fructus, Galli stomachichum corium, Trichosanthis radix, Rhei rhizoma, Dioscoreae rhizoma, Alisma rhizoma, Polygoni multiflori radix, Galla rhois, Formica fusca L., Sanchi ginseng,* Margaritum and Gecko.

5. The composition for treatment of diabetes according to claim 4, wherein as the supplementary natural drugs each of *Liriopsis tuber, Adenophorae radix, Trichosanthis radix, Cistanchis herba, Salviae radix, Polygoni multiflori radix, Mori radicis cortex, Anemarrhenae rhizoma, Alisma rhizoma, Schizandrae fructus, Pachymae fungus, Formica fusca L., Galli stomachichum corium, Phellodendri cortex* and Gecko is added in the ratio of 5–15 parts by weight; each of *Ginseng radix rubra, Rhei rhizoma* and *Galla rhois* is added in the ratio of 1–10 parts by weight; each of Margaritum and *Sanchi ginseng* is added in the ratio of 0.5–5 parts by weight; and *Dioscoreae rhizoma* is added in the ratio of 10–20 parts by weight.

6. The composition for treatment of diabetes according to claim 5, wherein as the supplementary natural drugs each of *Liriopsis tuber, Adenophorae radix, Trichosanthis radix, Cistanchis herba, Salviae radix, Polygoni multiflori radix, Mori radicis cortex, Anemarrhenae rhizoma, Alisma rhizoma, Schizandrae fructus, Pachymae fungus, Formica fusca L., Galli stomachichum corium, Phellodendri cortex* and Gecko is added in the ratio of 8–12 parts by weight; each of *Ginseng radix rubra, Rhei rhizoma* and *Galla rhois* is added in the ratio of 3–7 parts by weight; each of Margaritum and *Sanchi ginseng* is added in the ratio of 2–3 parts by weight; and *Dioscoreae rhizoma* is added in the ratio of 13–18 parts by weight.

7. The composition for treatment of diabetes according to claim 1, which is in the oral dosage form.

8. The composition for treatment of diabetes according to claim 7, wherein the oral dosage form is pill, tablet, capsule, solution or suspension.

9. A method for treating diabetes, comprising administering a therapeutically effective amount of the composition of claim 1, and a pharmaceutically acceptable carrier, to a person in need thereof.

10. The method of claim 9, wherein said diabetes is Type I diabetes.

11. The method of claim 9, wherein said diabetes is Type II diabetes.

* * * * *